United States Patent [19]

Price

[11] 4,336,135
[45] Jun. 22, 1982

[54] SUBMERGED ANAEROBIC FILTER WASTE TREATMENT APPARATUS

[76] Inventor: Richard H. Price, 161 Jefferson Ave., Memphis, Tenn. 38103

[21] Appl. No.: 926,918

[22] Filed: Jul. 21, 1978

[51] Int. Cl.³ ............................................. B01D 21/02
[52] U.S. Cl. ................................... 210/151; 210/256; 210/260
[58] Field of Search ............. 210/17, 150, 151, 195 R, 210/256, 260, 295, 615, 195.1

[56] References Cited

U.S. PATENT DOCUMENTS

| | | | |
|---|---|---|---|
| 3,567,629 | 3/1971 | Ayers et al. | 210/151 X |
| 3,850,810 | 11/1974 | Teodoroiu | 210/256 X |
| 4,055,490 | 10/1977 | Hasegawa et al. | 210/151 X |
| 4,069,156 | 1/1978 | Mason | 210/256 X |

*Primary Examiner*—Peter A. Hruskoci
*Attorney, Agent, or Firm*—Walker & McKenzie

[57] ABSTRACT

An apparatus for anaerobically treating waste to allow the waste to be safely disposed of and/or to reclaim useful gas therefrom. The apparatus includes a tank, a cylinder positioned within the tank to divide the tank into first and second areas, and media such as stones or the like positioned within the first and second areas of the tank for supporting anaerobic bacteria growth. Liquid waste is introduced into the first area of the tank over the media therein. As the waste flows through the media, the waste will be partially treated and methane gas or nitrogen gas will be formed or reclaimed therefrom. As more waste is introduced into the first area of the tank over the media therein, waste that has passed through the media in the first area will be forced upward through the media in the second area where it is further treated. Waste that has passed upwardly through the media in the second area of the tank is removed from the apparatus. The bottom edge of the cylinder is flared outwardly and downwardly to direct any gas formed when the waste passes through the media in the first area of the tank back upwardly through the media in the first area of the tank. After such gas passes upwardly through the media in the first area of the tank, it can be collected or it can be allowed to pass to the atmosphere.

10 Claims, 4 Drawing Figures

SUBMERGED ANAEROBIC FILTER WASTE TREATMENT APPARATUS

BACKGROUND OF THE INVENTION

1. Field of the Invention

This invention relates generally to apparatuses for treating liquid wastes and more specifically to such devices of the submerged anaerobic filter type.

2. Description of the Prior Art

Heretofore, various apparatuses have been developed for treating liquid wastes. See, for example, Booth, U.S. Pat. No. 2,274,658; Hagen, U.S. Pat. No. 2,948,400; Southworth, U.S. Pat. No. 3,118,834; and Cox, U.S. Pat. No. 3,279,606. None of the above patents disclose or suggest the present invention. In general, waste treatment apparatuses of the submerged anaerobic filter type have heretofore depended on the waste being introduced into the bottom of the media and forced upwardly through the media.

SUMMARY OF THE INVENTION

The present invention is directed towards improving upon prior anaerobic filter waste treatment apparatuses. The concept of the present invention is to provide an anaerobic waste treatment apparatus in which waste first flows downwardly through a first area of media means wherein methane and/or other gasses are produced therefrom and the remaining waste is then forced upwardly through a second area of media means which further treats the waste while the gas is directed upwardly back through the first area of media means.

The apparatus of the present invention includes, in general, a tank having a substantially closed bottom and a continuous side wall; cylinder means for dividing the interior of the tank into first and second areas, the cylinder means being opened and including a continuous side wall, the side wall of the cylinder means being spaced inwardly from the side wall of the tank to divide the interior of the tank into a first area located inside the side wall of the cylinder means and into a second area located outside the side wall of the cylinder means, the bottom edge of the side wall of the cylinder means being flared outwardly and downwardly towards the side wall and the bottom of the tank; media means for supporting anaerobic bacteria growth, the media means being located in the first and second areas of the tank; distribution means for introducing waste into the first area of the tank; and, outlet means for allowing treated waste to exit the tank, the outlet means being positioned within the second area of the tank above the media means.

DESCRIPTION OF THE PREFERRED EMBODIMENT

Figure 1:
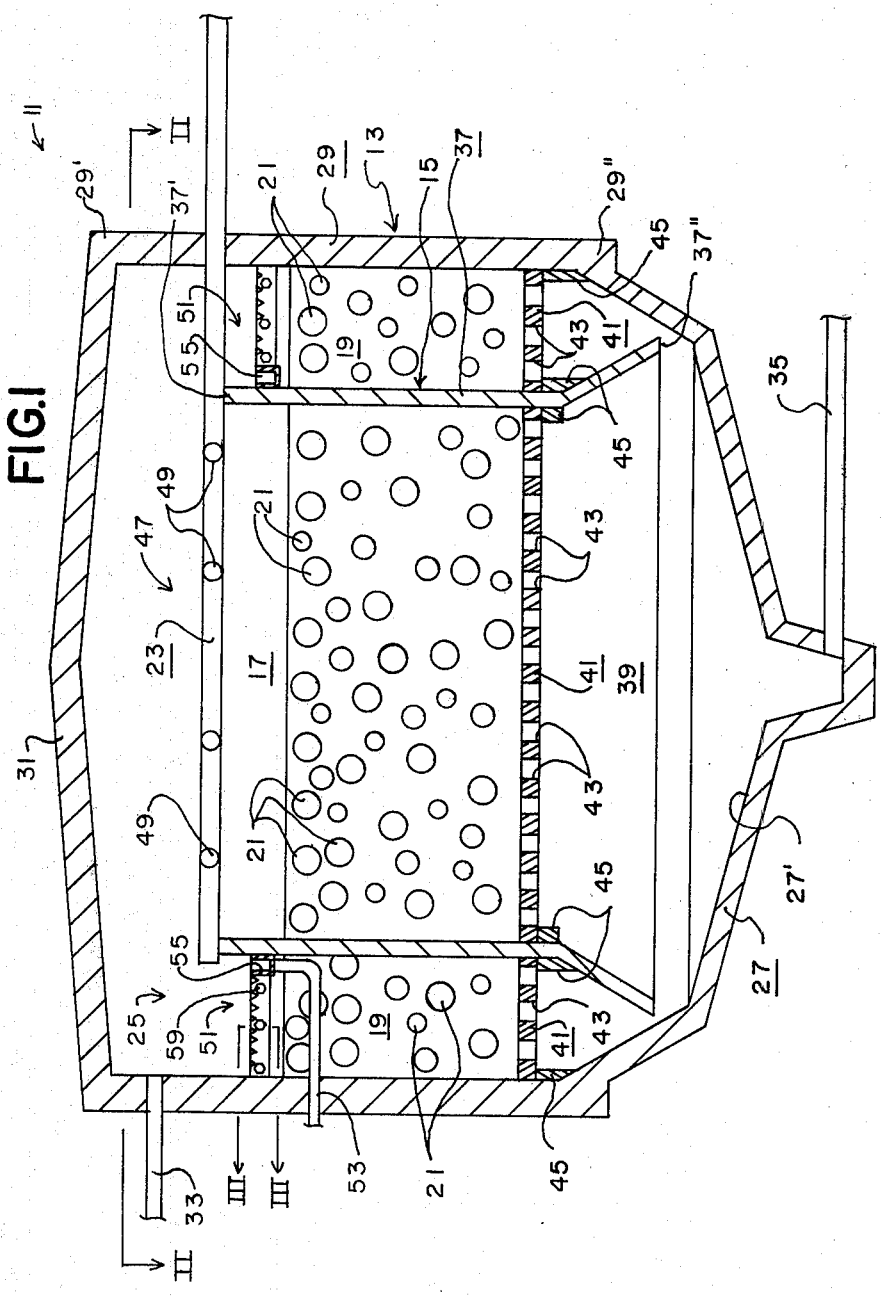
FIG. 1 is a sectional view of the waste treatment apparatus of the present invention.

The anaerobic waste treatment apparatus 11 of the present invention is for use in treating waste, especially wastes such as that created by food processing and other industrial processes or for removing nitrogen from wastes containing nitrogen in the nitrate form. The apparatus 11 may be used alone or in conjunction with other waste treating apparatuses. In general, the apparatus 11 includes a tank 13, a cylinder means 15 for dividing the tank 13 into a first area 17 and a second area 19, media means 21 located in the first and second areas 17, 19 of the tank 13, distribution means 23 for introducing waste into the first area 17 of the tank 13, and outlet means 25 for allowing treated waste to exit the second area 19 of the tank 13.

The tank 13 has a substantially closed bottom 27 and a continuous side wall 29. The side wall 29 has a top edge 29′ and a bottom edge 29″. The bottom edge 29″ is attached to the bottom 27 of the tank 13 and preferably forms an integral, one-piece unit therewith as shown in FIG. 1. The interior of the tank 13 is divided into the first and second areas 17, 19 by the cylinder means 15 in a manner and for reasons which will hereinafter become apparent. The tank 13 may be provided with a top 31 for trapping gas formed during the treatment of waste in the apparatus 11. The top 31 may be movably or floatingly positioned adjacent the top edge 29′ of the side wall 29 of the tank 13 in a manner and for reasons apparent to those skilled in the art. On the other hand, the top 31 may be fixedly attached to the top edge 29′ of the side wall 29 to form an integral, one-piece unit therewith as shown in FIG. 1. When the tank 13 is provided with the top 31, means for allowing any gas trapped therein to exit the interior of the tank 13 such as a pipe 33 through the side wall 29 of the tank 13 adjacent the top edge 29′ thereof is provided. Such means may be provided with means such as a compressor or the like to positively draw gas from the interior of the tank 13. Further, when the tank 13 is provided with the top 31, the tank 13 is also provided with appropriate gas safety apparatuses such as pressure relief devices, flame traps, and the like in a manner and for reasons apparent to those skilled in the art. The bottom 27 of the tank 13 may have an inwardly and downwardly sloping upper surface 27′ as shown in FIG. 1. A sludge withdrawal means such as a pipe 35 may be attached to the bottom 27 of the tank 13 at substantially the lowest point of the upper surface 27′ thereof for allowing withdrawal of any sludge or the like that may accumulate there when the apparatus 11 is in operation. The inwardly and downwardly slope of the upper surface 27′ of the bottom 27 of the tank 13 will direct any sludge or the like that may form within the tank 13 towards the lowest point thereof where it can be withdrawn through the pipe 35 in any manner apparent to those skilled in the art. The tank 13 may be constructed in any manner and of any material apparent to those skilled in the art. More specifically, the tank 13 may be cast out of concrete, molded out of metal, or the like.

The cylinder means 15 is opened at both ends and includes a continuous side wall 37 having a top edge 37′ and a bottom edge 37″. The side wall 37 of the cylinder means 15 is spaced inwardly from the side wall 29 of the tank 13 as clearly shown in FIGS. 1 and 2 to divide the interior of the tank into the first area 17 located inside the side wall 37 of the cylinder means 15 and into the second area 19 located between the side wall 37 of the cylinder means 15 and the side wall 29 of the tank 13. The bottom edge 37″ of the side wall 37 is flared outwardly and downwardly toward the side wall 29 and the bottom 27 of the tank 13 to form a skirt 39. The cylinder means 15 is suspended within the interior of the tank 13 with the bottom edge 37" thereof positioned slightly above the upper surface 27' of the bottom 27 of the tank 13 as clearly shown in FIG. 1. The cylinder means 15 may be so suspended within the tank 13 by any means known to those skilled in the art. For example, the cylinder means 15 may be supported by the support members 45.

Figure 2:
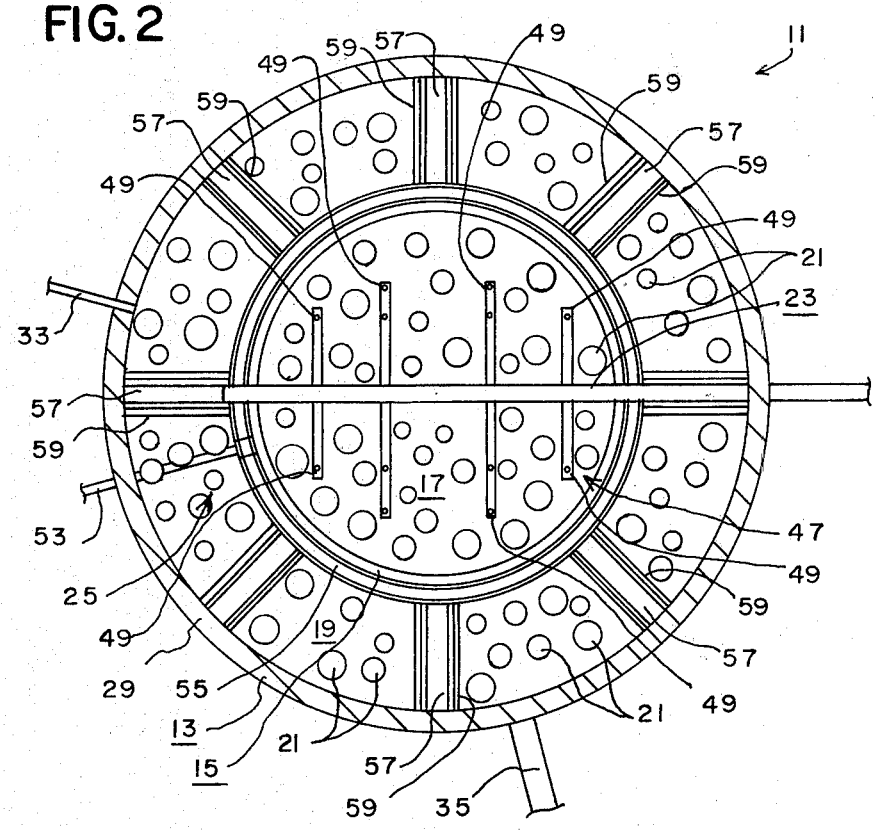
FIG. 2 is a sectional view as taken on line II—II of FIG. 1.

The media means 21 may consist of any well known structure for supporting anaerobic bacteria growth. For example, the media means 21 may consist of a plurality of stones, plastic sheet media, or synthetic random dump media or the like which allow anaerobic bacteria to grow on the media surfaces and in the spaces between under the proper conditions. The media means 21 is located in the first and second areas 17, 19 of the tank 13 as shown in FIGS. 1 and 2. The apparatus 11 preferably includes media support means 41 attached to the tank 13 and to the cylinder means 15 for supporting the media means 21 within the first and second areas 17, 19 of the tank 13 above the bottom 27 of the tank 13. The media support means 41 has a plurality of apertures 43 therethrough of a size that will allow waste to pass therethrough while preventing the media means 21 from passing therethrough. The media support means 41 may be suspended within the tank 13 and the cylinder means 15 in any manner apparent to those skilled in the art. For example, support members 45 may be fixedly attached to the side walls 29, 37 of the tank 13 and cylinder means 15 as shown in FIG. 1 for supporting the media support means 41. The media support means 41 may be constructed of a substantially rigid metal plate having a plurality of apertures formed therethrough, or the like.

The distribution means 23 has an outlet end 47 positioned so as to introduce waste into the first area 17 of the tank 13. The outlet end 47 of the distribution means 23 is positioned substantially adjacent the top edge 37' of the side wall 37 of the cylinder means 15 as shown in FIG. 1. The outlet end 47 of the distribution means 23 preferably includes a plurality of distribution arms 49 each equipped with outlet parts 49' substantially evenly distributed above the media means 21 within the first area 17 of the tank for substantially evenly introducing waste into the first area 17 of the tank 13.

Figure 3:
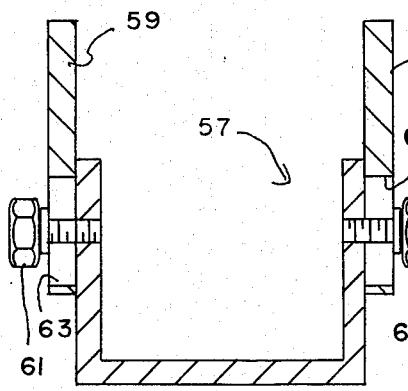
FIG. 3 is a sectional view as taken on line III—III of FIG. 1.
Figure 4:
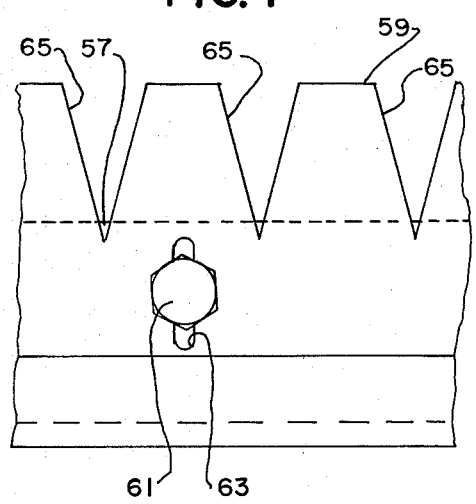
FIG. 4 is a side elevational view of the portion of the waste treatment apparatus shown in FIG. 3.

The outlet means 25 is positioned within the second area 19 of the tank 13 above the media means 21 therein for allowing treated waste to exit the tank 13. The outlet means 25 preferably includes an upwardly directed trough means 51 positioned within the second area 19 of the tank 13 above the media means 21 therein for receiving treated waste after the treated waste has risen above the media means 21 in the second area 19 of the tank 13. The outlet means 25 also preferably includes an outlet port member 53 coupled to the trough means 51 for allowing the treated waste received in the trough means 51 to exit the tank 13. The trough means 51 preferably includes a collector trough member 55 positioned within the second area 19 of the tank 13 and attached to the side wall 37 of the cylinder means 15 as shown in FIG. 1. The trough means 51 also preferably includes a plurality of radial launder members 57 positioned within the second area 19 of the tank 13 and extending between the side wall 29 of the tank 13 and the collector trough member 55. The outlet means 25 also may include weir means 59 attached to each of the launder members 57 for uniformly collecting the flow of treated waste into the trough means 51 in a manner as should be apparent to those skilled in the art. More specifically, the weir means 59 may be adjustably mounted to the launder members 57 by way of the bolts 61 and the slots 63 as clearly shown in FIGS. 3 and 4, and may have notches 65 in the top edges thereof so that when they are moved up or down relative to the launder members 57, the flow of treated waste into the launder members 57 may be equalized in a manner as should now be apparent to persons skilled in the art.

In the operation of the anaerobic waste treatment apparatus 11, liquid waste is fed into the first area 17 of the tank 13 above the media means 21 therein by way of the distribution means 23. The waste then flows downwardly through the media means where it is acted upon by anaerobic bacteria present within the media means 21. It should be noted that anaerobic bacteria is developed within the media means 21 in any manner apparent to those skilled in the art. As the waste exits the media means 21 in the first area 17 of the tank 13, it has been partially treated and much of the organic matter in the waste has been converted into carbon dioxide and methane gases, or much of the nitrates have been converted to nitrogen gas, depending on the intended function and biological process employed. The remaining waste will flow upwards around the skirt 39 of the cylinder means 15 and through the media means 21 in the second area 19 of the tank 13 due to the continued flow of waste into the first area 17 by the distribution means 23. Substantially all of the gases formed when the waste passes through the media means 21 in the first area 17 will be directed back through the media means 21 in the first area 17 of the tank 13 by the skirt 39 and the fact that gases so formed are lighter in weight than the waste passing down through the media means 21 in the first area 17 (i.e., the gases will bubble up through the waste passing down through the media means 21 in the first area 17 in a manner as should now be apparent to persons skilled in the art) and will pass through the media means 21 in the first area 17 to the top of the tank 13 where it is drawn off by the pipe 33 or passes to atmosphere, etc. The remaining waste is again subjected to anaerobic bacteria action as it passes upwardly through the media means 21 in the second area 19 of the tank 13. After the waste has passed through the media means 21 in the second area 19, it will flow into the trough means 51 and out of the tank 13 through the outlet port member 53 thereby completing the treatment of the waste in the apparatus 11.

Although the invention has been described and illustrated with respect to a preferred embodiment thereof, it is not to be so limited since changes and modifications may be made therein which are within the full intended scope of the invention.

I claim:

1. An anaerobic waste treatment apparatus for removing organic matter from waste, said apparatus comprising:
   (a) a tank including a substantially closed bottom and a continuous side wall having a bottom edge attached to said substantially closed bottom and having a top edge, said tank having an interior, said interior being divided into first and second areas;
   (b) cylinder means for dividing said interior of said tank into said first and second areas, said cylinder means being opened and including a continuous side wall having a top edge and a bottom edge, said continuous side wall of said cylinder means being spaced inwardly from said continuous side wall of said tank to divide said interior of said tank into said first area located inside of said continuous side wall of said cylinder means and into said second area located outside of said continuous side wall of said cylinder means, said bottom edge being flared outwardly and downwardly towards said continuous side wall and said substantially closed bottom of said tank;
(c) media means for supporting anaerobic bacteria growth, said media means being located in said first and second areas of said tank;
(d) distribution means for introducing said waste into said first area of said tank, for causing said waste to flow downwardly through said first area of said tank where said media means in said first area of said tank will cause much of said organic matter in said waste to be converted into gas, and for causing said waste to flow around said flared bottom edge of said cylinder means and upwardly through said second area of said tank, said flared bottom edge of said cylinder means directing said gas formed as said waste flows downwardly through said first area of said tank back upwardly through said first area of said tank;
(e) outlet means for allowing treated waste to exit said tank, said outlet means being positioned within said second area of said tank above said media means.

2. The anaerobic waste treatment apparatus of claim 1 in which said outlet means includes an upwardly directed trough means positioned within said second area of said tank above said media means for receiving treated waste after said treated waste has risen above said media means in said second area of said tank.

3. The anaerobic waste treatment apparatus of claim 2 in which said outlet means includes an outlet port member coupled to said trough means for allowing said treated waste received in said trough means to exit said tank.

4. The anaerobic waste treatment apparatus of claim 3 in which said trough means includes a collector trough member positioned within said second area of said tank and attached to said side wall of said cylinder means above said media means in said second area of said tank, and in which said trough means includes a plurality of radial launder members positioned within said second area of said tank and extending between said side wall of said tank and said collector trough member.

5. The anaerobic waste treatment apparatus of claim 4 in which said outlet means includes weir means attached to each of said launder members for controlling distribution of the flow of said treated waste into said trough means.

6. The anaerobic waste treatment apparatus of claim 5 in which said outlet end of said distribution means includes a plurality of outlet ports substantially evenly distributed above said media means within said first area of said tank for substantially evenly introducing waste into said first area of said tank.

7. The anaerobic waste treatment apparatus of claim 6 in which is included media support means attached to said tank and said cylinder means for supporting said media means within said first and second areas of said tank and above said bottom of said tank, said media support means having a plurality of apertures therethrough of a size that will allow said waste to pass therethrough while preventing said media means from passing therethrough.

8. The anaerobic waste treatment apparatus of claim 7 in which said bottom of said tank has an inwardly and downwardly sloping upper surface, and in which is included a sludge withdrawal means attached to said bottom of said tank substantially at the lowest point of said upper surface of said bottom of said tank for allowing withdrawal of any sludge that may accumulate there.

9. The anaerobic waste treatment apparatus of claim 8 in which said tank includes a top member for substantially covering said top edge of said side wall of said tank, and in which is included a gas draw off means for removing gas from said tank.

10. The anaerobic waste treatment apparatus of claim 9 in which said top member of said tank is fixedly attached to said top edge of said side wall of said tank.

\* \* \* \* \*